US006781921B2

(12) United States Patent
Markart

(10) Patent No.: US 6,781,921 B2
(45) Date of Patent: Aug. 24, 2004

(54) WRISTWATCH WITH MEASURING FUNCTION

(75) Inventor: Ernst Markart, München (DE)

(73) Assignee: LRE Technology Partner GmbH, Munich (DE)

( * ) Notice: Subject to any disclaimer, the term of this patent is extended or adjusted under 35 U.S.C. 154(b) by 0 days.

(21) Appl. No.: 10/458,858

(22) Filed: Jun. 11, 2003

(65) Prior Publication Data

US 2003/0231552 A1 Dec. 18, 2003

(30) Foreign Application Priority Data

Jun. 14, 2002 (DE) ........................................ 102 26 580

(51) Int. Cl.[7] ........................... G04B 47/00; A61M 5/00
(52) U.S. Cl. .......................... 368/10; 600/309; 600/322
(58) Field of Search ...................... 368/10; 600/309.322

(56) References Cited

U.S. PATENT DOCUMENTS 5,925,021 A * 7/1999 Castellano et al. ......... 604/207
6,180,063 B1 * 1/2001 Markart .................. 422/82.05
6,315,951 B1 * 11/2001 Markart ...................... 422/61
6,529,754 B2 * 3/2003 Kondo ...................... 600/344

FOREIGN PATENT DOCUMENTS

DE 296 03 371 U1 3/1997
EP 0 777 123 A2 6/1997

* cited by examiner

*Primary Examiner*—Vit W. Miska
(74) *Attorney, Agent, or Firm*—McCormick, Paulding & Huber LLP

(57) ABSTRACT

In a wristwatch including a housing, a time measuring device (32), a test measuring device (34) for a measuring by way of electric current a test strip (24) which has at least one test field wetable by a liquid to be investigated, and an indicator device (14) connected with the time measuring device (32) and test measuring device (34), a band holding member (38) is releasably connected to the housing and is oriented parallel to a housing outer surface (28), and together with the housing outer surface (28) forms a receiving opening (40) for holding a test strip (24) in a pre-given position, with the housing outer surface (28) having at least two measuring contact elements (50) connected with the test measuring device (34) for contacting electrodes of the test strip (24) and so arranged that their free ends protrude into the receiving opening (40).

20 Claims, 3 Drawing Sheets

12
16
18
10
44
II
24
44
II
14
20
22

30
48
24
50
62
50
52
52
56
56
46
56
28
56
44
54
44
54
66
58
66
54
38
54

WRISTWATCH WITH MEASURING FUNCTION

CROSS REFERENCE TO PRIOR APPLICATION

Applicant hereby claims foreign priority under 35 U.S.C. §119 from German Application No 102 26 580.1 filed 14 Jun. 2002, the disclosure of which is herein incorporated by reference.

FIELD OF THE INVENTION

The invention concerns a wristwatch including a housing, a time measuring device, a test measuring device for measuring by way of electric currents a test strip which has at least one test field wetable by a fluid to be investigated, and an indicating device connected with the time measuring device and the test measuring device.

BACKGROUND OF THE INVENTION

One such wristwatch is known for example from EP 777 123 A2. In this known wristwatch, the strip receiver for the insertion of the test strip is applied to a portion of the housing which protrudes laterally over the wristband of the watch. This has the disadvantage that the receiver is very difficult to clean. A dirtying of the strip receiver and of the measuring contacts which extend into the strip receiver can however lead to false measurements.

From DE 29 620 371 U1 is further known a wristwatch combined with a blood sugar measuring device. In one of the examples described there the wristwatch includes a lower housing part and a upper housing part, which are relatively movable to one another. In the lower housing part, the time measuring device and the test measuring device are brought together with the measuring optic system. In the upper housing part is arranged the indicator device which is connected by associated conductors with the measuring devices arranged in the lower housing part. On the upper surface of the lower housing part facing the upper housing part a strip receiver is formed into which can be laid a test strip wetted with the liquid to be investigated. In this case, there exists basically the possibility that by opening or moving away the housing parts the strip receiver can be laid free to allow carefully cleaning of the housing parts. However, this solution is relatively expensive especially in regard to assuring a secure and lasting electrical connection between the two relatively moveable housing parts.

SUMMARY OF THE INVENTION

The invention has its as its object the provision of a wristwatch of the previously mentioned kind which spacing saving and unobtrusively joins the functions of a watch and a test strip measuring device, which is simple in construction, and in the case of which the strip receiver can be reliably cleaned.

This object is solved in accordance with the invention in that a wristband holding member is releasably connected with the housing, is oriented parallel to a housing outer surface, and together with the housing outer surface defines a receiving opening for holding a test strip in a pre-given position, and that in the mentioned housing outer surface at least two measuring contact elements connected with the test measuring device are so arranged that they extend with their free ends into the receiving opening for contact with electrodes in the test field.

The solution according to the invention has the advantage that the time measuring device and the test measuring device as well as the indicator device all are arranged in the closed watch housing. Only the measuring contact elements extend out of the housing so as to be able to contact the electrodes in the test field. The band holding member serves only to hold the test strip in the position required for a correct contacting, with the band holding member at any time being removable from the housing to be able to clean the contacts and the surrounding housing surfaces as well as the band holding member without trouble. The watch can also be used without the band holding member in which case it is practically indistinguishable from a customary digital watch.

If it makes no difference that the band holding member remain on the housing, it can also for example be joined by a hinge to the housing so that it can easily be swung away from the associated housing surface. Also guide members for the test strips which sidewise guide the strips and/or limit their insertion depth, can be formed on the associated housing surface.

Preferably the measuring contact element containing housing outer surface is that of the housing bottom. On one hand the measuring contact elements on the housing are inconspicuous, and on another hand the housing bottom offers a relatively large surface to which to apply the band holding member and which can assure a reliable guiding of the test strip. If the band holding member is a plate which surfacewise nearly matches the housing bottom, in the wearing of the wristwatch the band holding member is practically inconspicuous.

To ease application and removal of the band holding member to and from the housing, the band holding member is prefereably connectable with the housing by means of clip connectors, so that no tools are necessary to connect or disconnect the band holding member to or from the housing. For example, the clip connectors can include detent protrusions on the band holding member and detent openings in the housing designed to receive the detent protrusions. This solution has the advantage that on the watch housing itself no protruded parts are provided which can disturb the wearer of the wristwatch when the band holding member is not connected with the housing.

If the housing of the wristwatch is made of metal, it is advantageous if the measuring contact elements are arranged in an insulating part inserted into the mentioned housing outer surface. To assure a secure making of contact the insulating part can be resiliently deflectably supported in the receiving housing surface for movement perpendicularly to the housing surface, which insulating part in its fundamental position is lightly pressed outwardly with the measuring contact elements so they lie under resilient pressure onto the electrodes of the test field of a test strip inserted into the receiving opening.

To avoid a dirtying of the insulating part by the fluid under investigation and by the test chemicals, the insulating part is advantageously made of a hydrophobic material.

In place of the resilient support of the insulating part, or perhaps additionally thereto, a pressing element for pressing the test strip against the measuring contact elements can be provided on the band holding member. For example, the pressing element can be leaf spring which is either fastened to or made of one piece with the band holding member.

To assure that the contact elements are clean and that no moisture is contained in the receiving opening, which could falsify a measurement, in the region of the measuring contact elements a moisture sensor is preferably provided. This can be so made in that it includes an auxiliary contact and a resistance measuring device by means of which the electrical resistance between the auxiliary contact and at least one of the measuring contact elements is measurable. In association with an amplitude evaluating circuit, in the event of the falling below of a pre-given resistance value or upon the exceeding of a pre-given conductivity value, a signal can be created which informs the user that he should first clean and dry the receiving opening and the contact elements before making the next measurement.

The time measuring device and test measuring device can be alternately activatable, so that for example the indicating device can be used to show in full size the individual measurements. The arrangement can however be so made that at least one of the measuring devices, in general the time measuring device, is constantly active and that the other measuring device is selectively turned on. The switching between the measuring devices or the switching on of the selectively activatable measuring device can be accomplished by means of a switch which is arranged on the outer side of the housing. Another possibility exists in that the switching between the measuring devices or the switching on of the selectively activable measuring device takes place in dependence on the insertion or removal of a test strip into or out of receiving opening. As a sensor for detecting the insertion or removal of the test strip, a measuring contact element with or without an auxiliary contact can be used.

In the preferred solution of the invention the time measuring device and the test measuring device are formed as separate modules.

Preferably contacts are arranged on the housing outer surface to make possible a data exchange between the data processing unit of the test measuring device and an external device.

BRIEF DESCRIPTION OF THE DRAWINGS

Further features and advantages of the invention will be apparent from the following description which in combination with the accompanying drawings explain the invention by way of exemplary embodiments. The drawings are.

DETAILED DESCRIPTION OF THE PREFERRED EMBODIMENTS

Figure 1:
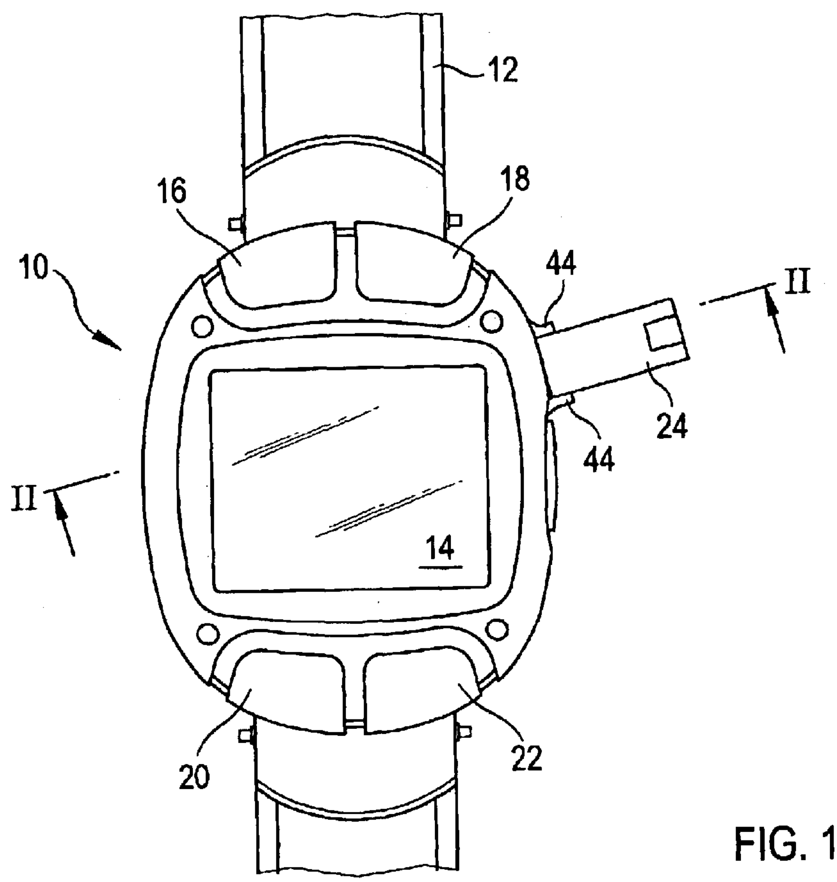
FIG. 1 A schematic plan view of a watch embodying the invention.

In FIG. 1 is seen a wristwatch with a watch housing 10 to which a wrist band 12 is fastened. On the upper side of the watch housing 10 is an LCD-screen 14 of an indicating device. Both above and below the LCD screen 14 are two operating keys 16, 18 and 20, 22 for actuating and controlling various functions of the illustrated wristwatch. As is explained below in more detail, in addition to a time measuring device the watch also includes a measuring device for the electrical current measurement of test strips 24, which in known ways include a test field which can be wetted with a liquid to be investigated, for example blood, to determine the concentration of given substances, for example glucose, in the liquid.

Figure 2:
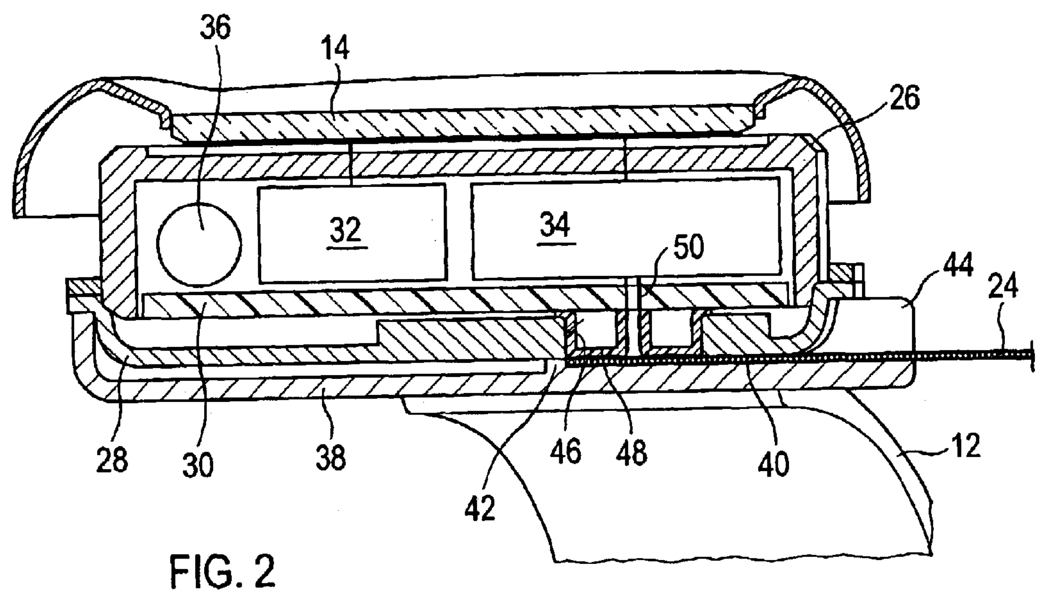
FIG. 2 A schematic cross-sectional view through the watch illustrated in FIG. 1 taken along the line II—II of FIG. 1, FIG. 3 A partial cross-sectional view corresponding to FIG. 2 taken through a somewhat modified embodiment of a watch embodying the invention, FIG. 4 An exploded view of the parts which form the lower portion of the watch illustrated in FIG. 3.

According to FIG. 2 the housing 10 has an upper housing part 26 and a housing bottom 28. Inside of the housing is a circuit board 30 on which is arranged a watch module 32 forming the time measuring device and a measuring module 34 forming the test strip measuring device. Next to this is indicated a current source in the form a battery 36. The modules 32, 34 are connected with the LCD screen 14.

Below the housing bottom 28 is a plate shaped band holding member 38, which is releasably connected with the housing 10 and which is explained in more detail later in connection with FIGS. 4 and 5. The band holding member 38 defines together with the housing bottom 28 a receiving opening 40 for the test strips 24. The receiving opening 40 is inwardly limited by a stop 42 for the test strips 24. Lateral guide portions 44 at the mouth of the receiving opening 40 facilitate the insertion of the test strips 24.

In the housing bottom 28 customarily made of metal a recess 46 is provided in which an insulating part 48 is inserted, which in turn contains contact elements 50 which are connected with the measuring module 34 and are designed to contact electrodes 52 (FIG. 4) on the test strip 24.

Figure 3:
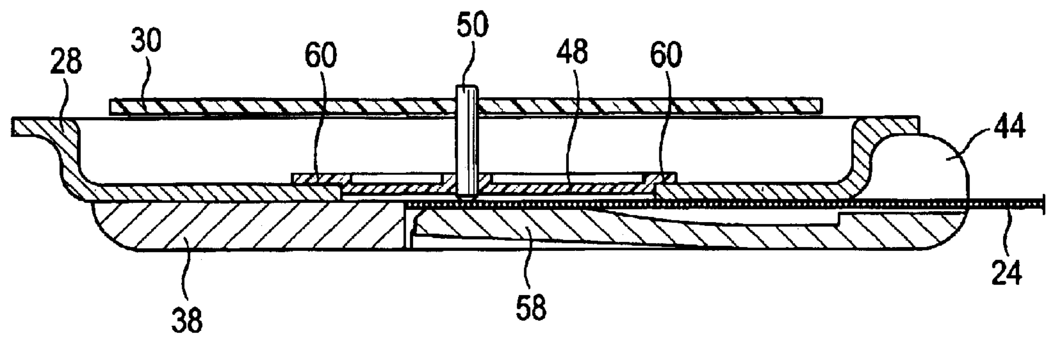
Figure 4:
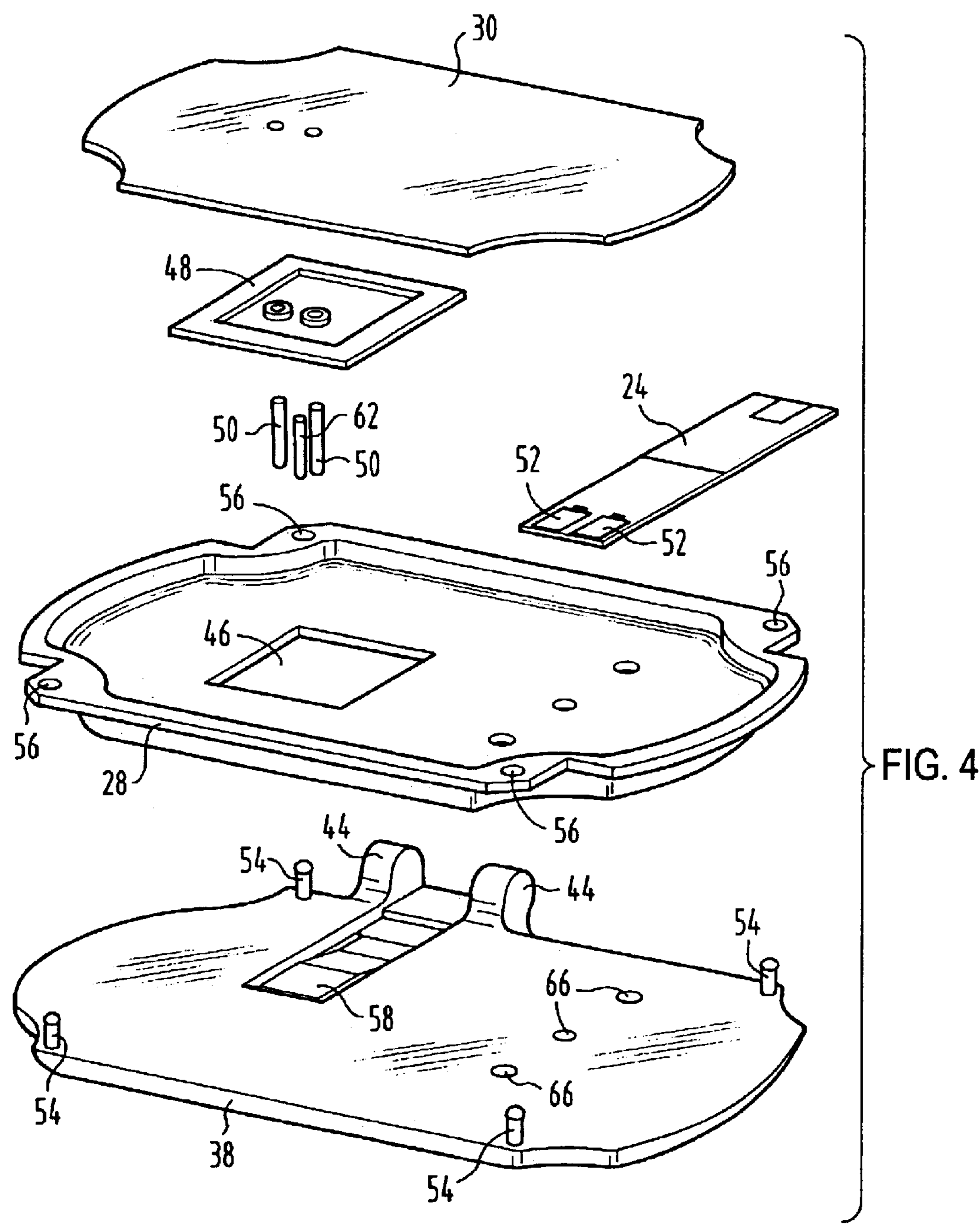

In FIGS. 3 and 4 are illustrated in more detail the parts for the holding and contacting of the test strips 24, with only the housing bottom 28 of the housing 10 being shown.

The connection of the housing bottom 28 with the band holding member 38 is achieved by way of clip or detent connectors. For this the band holding member 38 has on its side facing the housing bottom 28 four pins 54 which at their free ends are thickened and ball-shaped and designed for reception in corresponding detent openings 56 in the housing bottom 28. In this way the band holding member 38 can without difficulty and quickly be connected with or removed from the housing bottom 28.

The receiving opening 40 bounding surface of the band holding member 38 is formed by a tongue or flap 58 formed as one piece with the band holding member 38 and which has the function of a leaf spring and presses the strips 28 in the region of the electrodes 52 against the measuring contact elements 50 to assure a reliable contacting (FIG. 3). Alternatively to this or in addition to this the insulating member 48 can be so arranged in the opening 46 of the housing bottom 28 that it is at least slightly resiliently deflectable perpendicularly to the housing bottom 28. This can for example be assured by a rubber seal which can be arranged between the edge flange 60 of the insulating part 48 (FIG. 3) and the housing bottom 28.

In FIG. 4 an auxiliary contact 62 is illustrated between the measuring contact elements 50, which auxiliary contact is connected with at least one of the measuring contact elements 50 through a non-illustrated resistance measuring device within the measuring module 34. By a resistance measurement it can be determined whether the region of the housing bottom around the measuring contact elements 50 is clean and dry or is fouled by the measuring fluid. In the latter case a signal is produced by the indicator device which makes the user aware that he should clean the area surrounding the measuring contacts elements 50. This can be done without effort and quickly in that the band holding member 38 can be removed from the housing bottom 28 and the housing bottom 28 wiped off and dried.

In FIG. 4 contact points are indicated at 64 which on one hand are connected with the measuring module 34 and on the other hand extend through the housing bottom 28 to the outer or underside of the housing bottom 28 and therefore can be used to connect a data processing device within the measuring module 34 with an external data processing device. To make possible a contacting even when the band holding member 38 is connected with the housing bottom 28 openings 66 are provided in the band holding member which align with the contact points 64.

Figure 5:
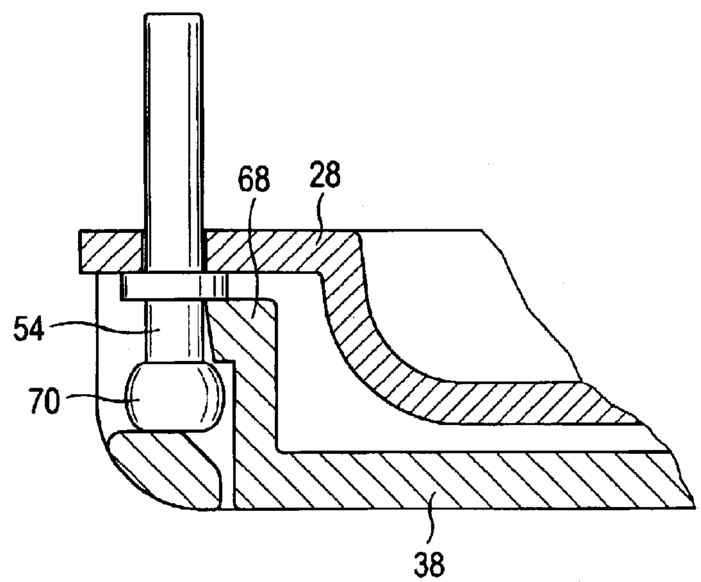
FIG. 5 A partial sectional view through a modified form of the clip connection between the band holder member and the watch housing, and FIG. 6 A schematic illustration of the display screen of the indicating device.

FIG. 5 shows in detail a detent connection explained above by way of FIG. 4, wherein the detent pins 54 are provided on the housing bottom 28 and the detent openings 56 are provided on the band holding member 38. It will be seen that a resiliently deflectable detent nose 68 is on the band holding member 38, which nose in the assembled condition is located behind the ball-shaped thickening 70 of the detent pin 54.

Figure 6:
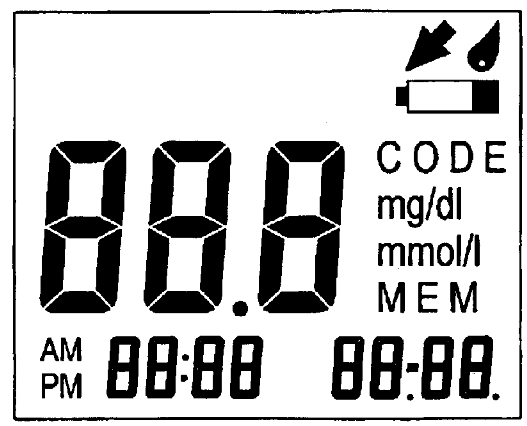

With the aid of the keys 16, 18, 20, 22 different functions of the illustrated wristwatch can be called up. In this way the measuring module 34 can be turned on by key pressings and the indicator switched to indicate the measuring results in addition to the indication of the time as illustrated in the FIG. 6, or the indicator can be switched from an indication of the time to an indication of the measuring results. Moreover with the keys one can control data exchange with an external device and can interrogate stored values. The storage condition of the battery can be indicated simultaneously with the measuring results and the time, as is likewise to be seen in FIG. 6. The given enumeration of the functions is only exemplary and not limiting.

The aforesaid description shows that the band holding member can be conveniently removed from the watch and that it is thereby possible to keep without trouble the receiving opening for the measuring strips clean and dry, which is absolutely necessary for exact measurements. At the same time the band holding member can also be removed if the measuring function of the wristwatch is not needed, without comfort disturbing parts of the housing bottom thereby being provided and without the danger existing that the measuring contact elements may be damaged.

What is claimed is:

1. A wristwatch including a housing (10), a time measuring device (32), a test measuring device (34) for measuring by way of electric currents a test strip (24) having at least one test field wetable by a liquid to be investigated, and an indicator device (14) connected with the time measuring device (32) and the test measuring device (34), characterized in that on the housing (10) is arranged a band holding member (38) which is releasably connected with the housing and is oriented parallel to a housing outer surface (28) and together with the housing outer surface (28) defines a receiving opening (40) for holding a test strip (24) in a pre-given position and that in the housing outer surface (28) are arranged at least two measuring contacts (50) which extend with their free ends into the receiving opening (40) and which electrodes are connected with the test measuring device (34) and are designed to contact electrodes (52) of the test strip (24).

2. A wristwatch according to claim 1, further characterized in that the housing outer surface having the measuring contacts (50) is that of the housing bottom (28).

3. A wristwatch according to claim 2 further characterized in that the band holding member (38) is a plate having a surface similar to that of the housing bottom (28).

4. A wristwatch according to claim 1, further characterized in that the band holding member (38) is connectable with the housing (10) by way of clip connectors (54, 56).

5. A wristwatch according to claim 4, further characterized in that the clip connectors include detent protrusions (54) on the band holding part member (38) and detent openings (56) in the housing (10) designed to receive the detent protrusions.

6. A wristwatch according to claim 1 further characterized in that the measuring contact elements (50) are arranged in an insulating part (48) inserted into the housing outer surface (28).

7. A wristwatch according to claim 6, further characterized in that the insulating part (48) is supported in the receiving housing surface (28) so as to be resiliently movable perpendicularly to the housing surface (28).

8. A wristwatch according to claim 6 further characterized in that the insulating part is made of a hydrophobic material.

9. A wristwatch according to claim 1 further characterized in that a pressing element is provided on the band holding member (38) for pressing the test field against the measuring contact elements (50).

10. A wristwatch according to claim 9 further characterized in that the pressing element is formed by a leaf spring (58).

11. A wristwatch according to claim 9 further characterized in that the pressing element is formed of one piece with the band holding member (38).

12. A wristwatch according to claim 1, further characterized in the region of the measuring contact elements (50) a moisture sensor is provided.

13. A wristwatch according to claim 12, further characterized in that the moisture sensor includes an auxiliary contact (62) and a resistance measuring device by means of which the electrical resistance between the auxiliary contact (62) and at least one of the measuring contact elements (50) is measurable.

14. A wristwatch according to claim 13, further characterized in that the resistance measuring device is connected with an amplitude measuring circuit which upon the falling below of a pre-given resistance value creates a signal.

15. A wristwatch according to claim 1, further characterized in that the time measuring device (32) and the test measuring device (34) are alternately activatable.

16. A device according to claim 1, further characterized in that at least one of the measuring devices (time measuring device 32, test measuring device 34) is continuously active and the other is capable of being selectively turned on.

17. A wristwatch according to claim 15, further characterized in that to switch between the measuring devices (32, 34) or to turn on the selectively activatable measuring device, a switch (16, 18, 20, 22) is arranged at the housing outer side.

18. A wristwatch according to claim 15, further characterized in that the switching between the measuring devices (32, 34) or the turning on of the selectively activatable measuring device takes place in dependence on the insertion or removal of a test strip (24) into or out of the receiving opening (40).

19. A wristwatch according to claim 1, further characterized in that the time measuring device (32) and the test measuring device (34) are formed as separate modules.

20. A wristwatch according to claim 1, further characterized in that the test measuring device (34) has a data processing unit which by way of contacts (64) arranged at the housing outer side can be connected to an external device for the exchange of data.

* * * * *